US009119645B2

(12) United States Patent
McBride (10) Patent No.: US 9,119,645 B2
(45) Date of Patent: Sep. 1, 2015

(54) PEDICLE DRILL GUIDE FOR SPINAL SURGERY

(75) Inventor: George Grady McBride, Winter Park, FL (US)

(73) Assignee: Amendia, Inc., Marietta, GA (US)

( * ) Notice: Subject to any disclaimer, the term of this patent is extended or adjusted under 35 U.S.C. 154(b) by 451 days.

(21) Appl. No.: 13/430,802

(22) Filed: Mar. 27, 2012

(65) Prior Publication Data

US 2012/0253353 A1 Oct. 4, 2012

Related U.S. Application Data

(60) Provisional application No. 61/468,310, filed on Mar. 28, 2011.

(51) Int. Cl.
  *A61B 17/17* (2006.01)
  *A61B 17/88* (2006.01)
  *A61B 17/00* (2006.01)

(52) U.S. Cl.
  CPC ......... *A61B 17/1757* (2013.01); *A61B 17/8897* (2013.01); *A61B 2017/0046* (2013.01)

(58) Field of Classification Search
  CPC .............. A61B 17/17; A61B 17/1757; A61B 17/1703; A61B 2017/0046
  USPC ..................................... 606/96–98
  See application file for complete search history.

(56) References Cited

U.S. PATENT DOCUMENTS

| | | | | |
|---|---|---|---|---|
| 2,725,053 A | * | 11/1955 | Bambara et al. | 606/96 |
| 4,441,492 A | * | 4/1984 | Rydell et al. | 606/67 |
| 4,545,374 A | * | 10/1985 | Jacobson | 600/210 |
| 5,147,367 A | * | 9/1992 | Ellis | 606/96 |
| 5,324,295 A | * | 6/1994 | Shapiro | 606/86 R |
| 5,489,284 A | * | 2/1996 | James et al. | 606/62 |
| 5,728,128 A | * | 3/1998 | Crickenberger et al. | 606/97 |
| 5,749,884 A | * | 5/1998 | Benderev et al. | 606/167 |
| 5,766,221 A | * | 6/1998 | Benderev et al. | 606/232 |
| 5,797,909 A | | 8/1998 | Michelson | |
| 5,951,561 A | * | 9/1999 | Pepper et al. | 606/80 |
| 6,669,698 B1 | * | 12/2003 | Tromanhauser et al. | 606/86 A |
| 7,422,594 B2 | * | 9/2008 | Zander | 606/80 |
| 7,840,254 B2 | | 11/2010 | Glossop | |
| 7,846,164 B2 | | 12/2010 | Castillo et al. | |
| 2003/0040753 A1 | * | 2/2003 | Daum et al. | 606/96 |
| 2003/0105461 A1 | * | 6/2003 | Putnam | 606/69 |
| 2003/0236527 A1 | * | 12/2003 | Kawakami | 606/96 |
| 2004/0215203 A1 | * | 10/2004 | Michelson | 606/96 |
| 2005/0021067 A1 | * | 1/2005 | Kim | 606/189 |
| 2006/0100637 A1 | * | 5/2006 | Rathbun et al. | 606/96 |
| 2007/0276397 A1 | | 11/2007 | Pacheco | |
| 2008/0021479 A1 | * | 1/2008 | Penenberg | 606/96 |
| 2008/0086144 A1 | * | 4/2008 | Zander | 606/96 |
| 2008/0269744 A1 | * | 10/2008 | Kay et al. | 606/62 |
| 2009/0088604 A1 | | 4/2009 | Lowry | |
| 2011/0015642 A1 | * | 1/2011 | Penenberg | 606/96 |

* cited by examiner

*Primary Examiner* — Zade Coley

(74) *Attorney, Agent, or Firm* — David L. King (57) ABSTRACT

A Pedicle Drill Guide is a radiolucent device which allows preliminary positioning of a needle/trochar near the pedicle in the AP view and adjusting the final position of the lateral view without changing the initial position of the AP position. This guide allows simultaneous alignment of both AP and Lateral views for ultimate ideal or perfect pathway for the pedicle cannulization.

15 Claims, 14 Drawing Sheets

PEDICLE DRILL GUIDE FOR SPINAL SURGERY

RELATED APPLICATIONS

The present application claims priority to U.S. Provisional Application 61/468,310 filed Mar. 28, 2011 entitled, "This is a surgical drill guide that is used to cannulate a vertebral pedicle for spinal surgery".

FIELD OF THE INVENTION

The present invention relates to a surgical drill guide that is used to cannulate a vertebral pedicle for spinal surgery.

BACKGROUND OF THE INVENTION

Pedicle screw implementation in the spine is a preferred way to provide superior anchorage. Improved deformity correction and overall construct rigidity are two important advantages of pedicle screw instrumentation due its three-column control over the spinal elements. First, pedicle screw instrumentation obviates the need to place instrumentation within the spinal canal with its inherent risk of neurologic injury. Second, the placement of pedicle screws is independent of facet or laminar integrity and thus has been extremely useful in traumatic, neoplastic, and degenerative conditions. The benefit of pedicle screws in the thoracic spine has been tempered by the potential for catastrophic neurological or soft tissue injuries due to the close proximity of these structures. The narrow and inconsistent shape of the thoracic pedicles, especially in spinal deformity, makes their placement technically challenging. As a result, surgeons have employed a number of techniques to ensure the safe and efficacious placement of thoracic pedicle screws. Detailed anatomic landmarks used to determine pedicle location, intraoperative imaging including navigation, and neurophysiological monitoring are some of the techniques currently used by surgeons. The implementation of these techniques and a thorough understanding of the complex three-dimensional anatomy have allowed surgeons to successfully place thoracic and thoracolumbar pedicle screws.

To facilitate accurate placement, a pedicle punch was developed by Castillo, et al as disclosed in U.S. Pat. No. 7,846,164. This device gave the user the ability to create an accurate pilot hole via a pointy tipped punch. This device when used in combination with the x-ray imaging technique facilitated the screw implant procedure in the spine by providing an initial pilot hole.

A secondary advantage was the exposure to radiation from x-ray imaging could be reduced. Castillo, et al noted, "Another drawback of the pedicle screw implant procedure is that the patient, surgeon, and medical staff are exposed to deleterious amounts of radiation, more specifically those deleterious amounts of radiation associated with fluoroscopy during the pedicle screw implant procedure. One way surgeons can protect themselves is with eyewear, thyroid shields, and lead aprons. However, studies with cadavers have shown that the surgeon's hands are still at a high risk of radiation exposure. In one study average fluoroscopy exposure time was 9.3 s per screw. and the average hand dose rate was 58.2 mrem/min. The internationally recommended maximum limit for annual hand radiation exposure is 50,000 mrem. In the same study a significant increase in hand dose rate was noted when placement of the screw was on the same side of the beam source as well as when a heavier cadaver was imaged."

The use of Castillo, et al's punch device was purported to lower this risk. This prior art punch device while a step forward still was greatly limited in screw placement optimization. The punch simply allowed for a pilot hole to be created at a fixed location. What the surgeon was lacking was the ability to optimally select a preferred location to insert the screw and to do so in a way that minimized bone fracture or damage.

Ideally, the surgeon needed a way to select an optimal location for screw placement based on the images he was seeing prior to fixing the location by creating the punched hole.

The present invention as described as follows provides a guide tool that allows the surgeon to optimally select a location for screw placement, create a secured guided location through which a K-wire placement can be placed to be fixed into the pedicle bone at a location selected by the surgeon.

SUMMARY OF THE INVENTION

A pedicle drill guide for use in spinal surgery to cannulate a vertebral pedicle is disclosed. The drill guide has a guide body adapted to receive a stabilizing anchor pin. The guide body extends longitudinally from an outer end to an inner tip end. The guide body has a center hole for receiving the stabilizing anchor pin. The center hole extends longitudinally through the outer end and inner tip end. A plurality of satellite holes extend through the guide body from inner tip end and outer end parallel to the center hole. Each satellite hole is spaced from the center hole by a distinct predetermined distance (d) and sized to receive a K-wire.

The K-wire when inserted in a satellite hole for placement into a pedicle is fixed at the distance (d) from the center of stabilizing anchor pin.

The guide body is rotatable about the stabilizing anchor pin to allow positioning and alignment of a satellite hole relative to the pedicle. The central stabilizing pin and rotating guide allows the surgeon to fix the medial-lateral position of the guide over the center or lateral center of the pedicle on the AP view while allowing for alignment of the pedicle central axis on the lateral view by rotating the guide body. The guide body has at least 2 satellite holes, preferably at least 3 satellite holes, most preferably 4. The plurality of satellite holes are spaced in 1 mm increments from the center hole. The first satellite hole is at 1 mm distance ($d_1$), a second satellite hole at 2 mm distance ($d_2$), a third satellite hole if used is at 3 mm distance ($d_3$) and a fourth satellite hole if used at 4 mm distance ($d_4$).

The pedicle drill guide has a removable handle with a split end for attachment to the guide body. The outer end of the guide body has an enlarged end with an outer gripping surface and a grooved channel adjacent the outer gripping surface for receiving the split end of the handle.

The guide body near the inner tip end has a truncated conical shaped tip for insertion into a surgical opening above the spine of the patient. The guide body is made of a plastic or any other material which allows x-ray imaging to pass. Preferably, the guide body is disposable and the material of the guide body is selected to be heat sensitive and not suitable for autoclave sterilization. The pedicle drill guide further has a target ring affixed to the guide body. The guide body has the target imaging grooved slot near the conical inner tip end to hold the target ring. The target ring is preferably made of a radiopaque metallic material. The inner tip end has a plurality of spiked projections for contacting the surface of the pedicle.

The satellite holes are sized with at least the portion near the inner end closely sized to the diameter of K-wire. The diameter of the K-wire is typically 1/16 of an inch and the satellite hole diameter at the inner end portion being slightly larger to allow a slip fitment. In a preferred embodiment, the diameter of the satellite holes is larger from the outer end and extending toward the inner portion of the hole, thereafter the diameter is reduced to about the size of the K-wire diameter or slightly larger for a close fit.

DEFINITIONS

As used herein and in the claims:

Kirschner wires or K-wires or pins are sterilized, sharpened, smooth stainless steel pins. Introduced in 1909 by Martin Kirschner, the wires are now widely used in orthopaedics and other types of medical and veterinary surgery. They come in different sizes and are used to hold bone fragments together (pin fixation) or to provide an anchor for skeletal traction. The pins are often driven into the bone through the skin (percutaneous pin fixation) using a power or hand drill.

The Jamshidi needle is a cylindrical needle with a tapered cutting tip. The tapered end reduces the potential of crush artifact.

BRIEF DESCRIPTION OF THE DRAWINGS

The invention is described by way of example and with reference to the accompanying drawings in which.

DETAILED DESCRIPTION OF THE INVENTION

Figure 5:
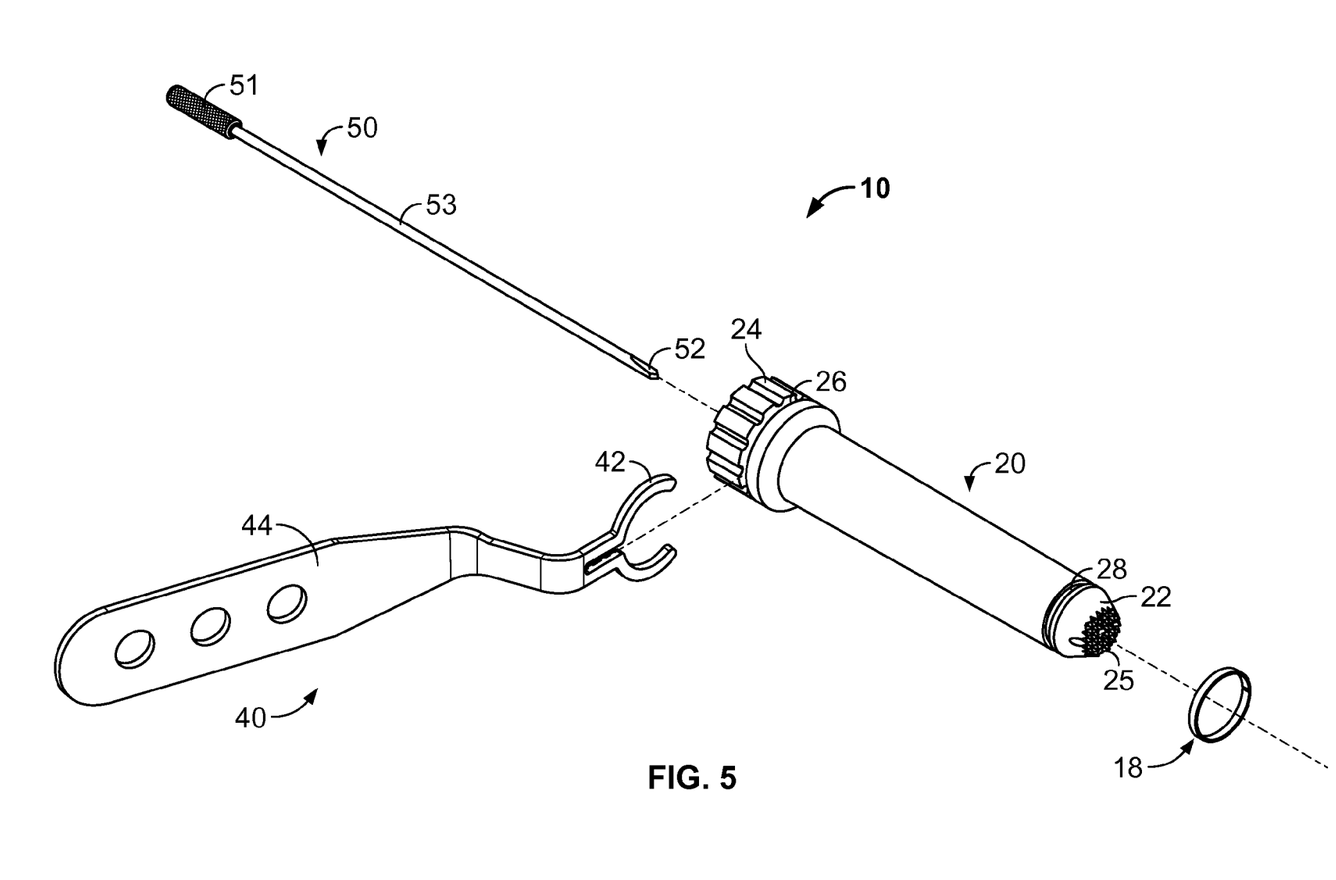
FIG. 5 is an exploded perspective view of the Pedicle Drill Guide device showing the guide body, stabilizing anchor pin, handle and image target ring.
Figure 6:
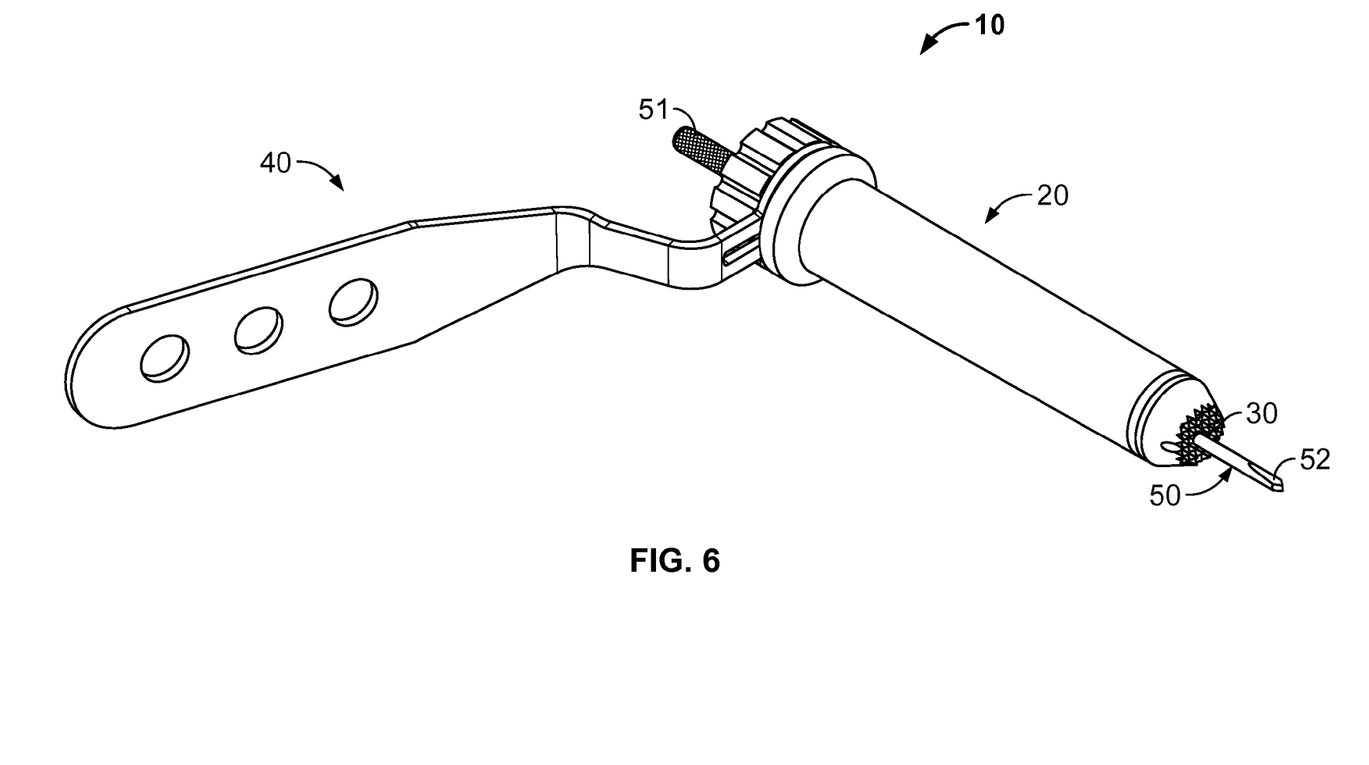
FIG. 6 is a perspective view of the Pedicle Drill Guide components of FIG. 5 assembled.
Figure 7:
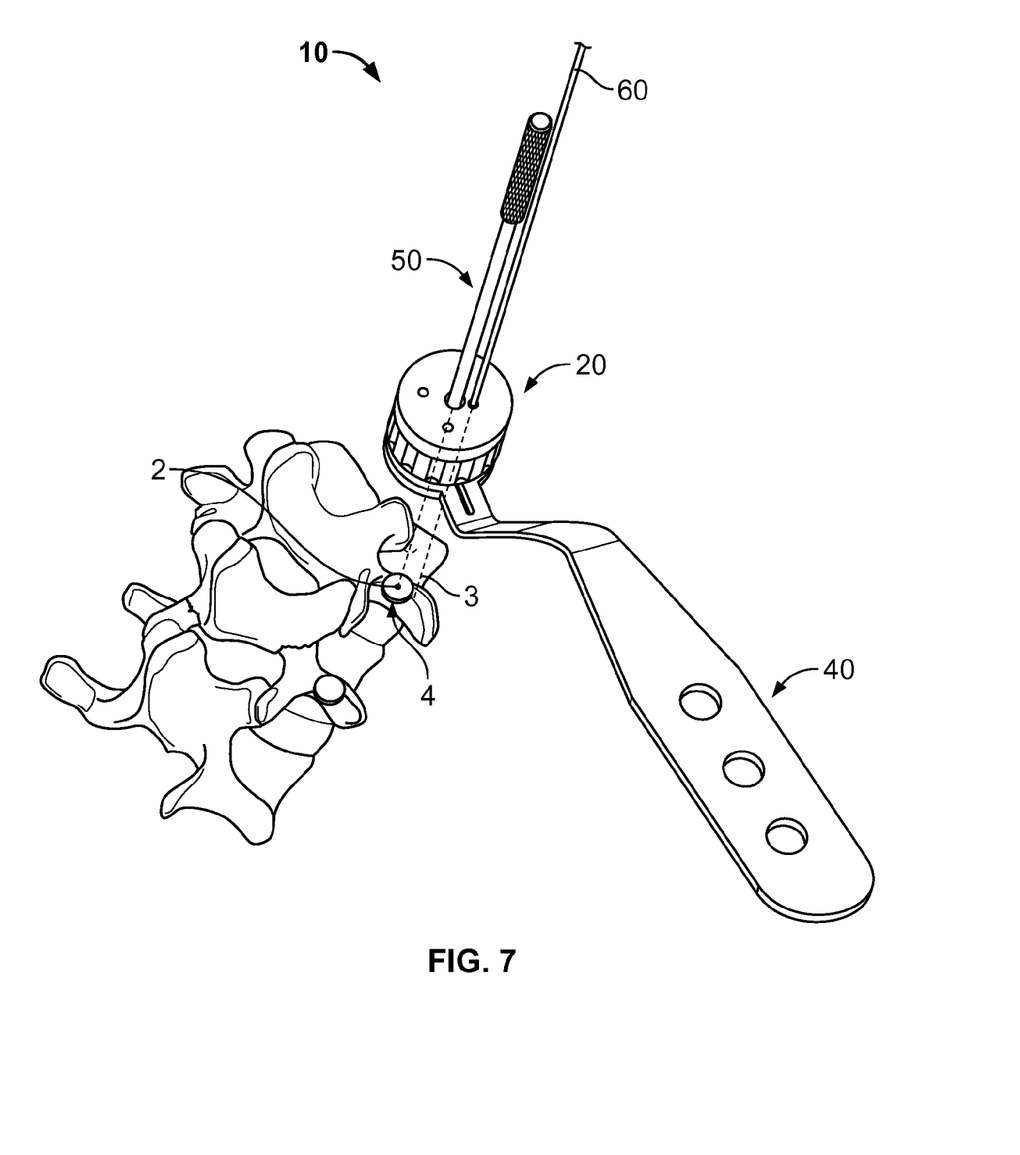
FIG. 7 is a perspective view of the device in use showing vertebra and the dashed lines depicting the location of the stabilizing anchor pin and the K-wire when directed by the guide body wherein the outer end of the guide body is shown with the remaining portion not shown to expose the bone structure.
Figure 7A:
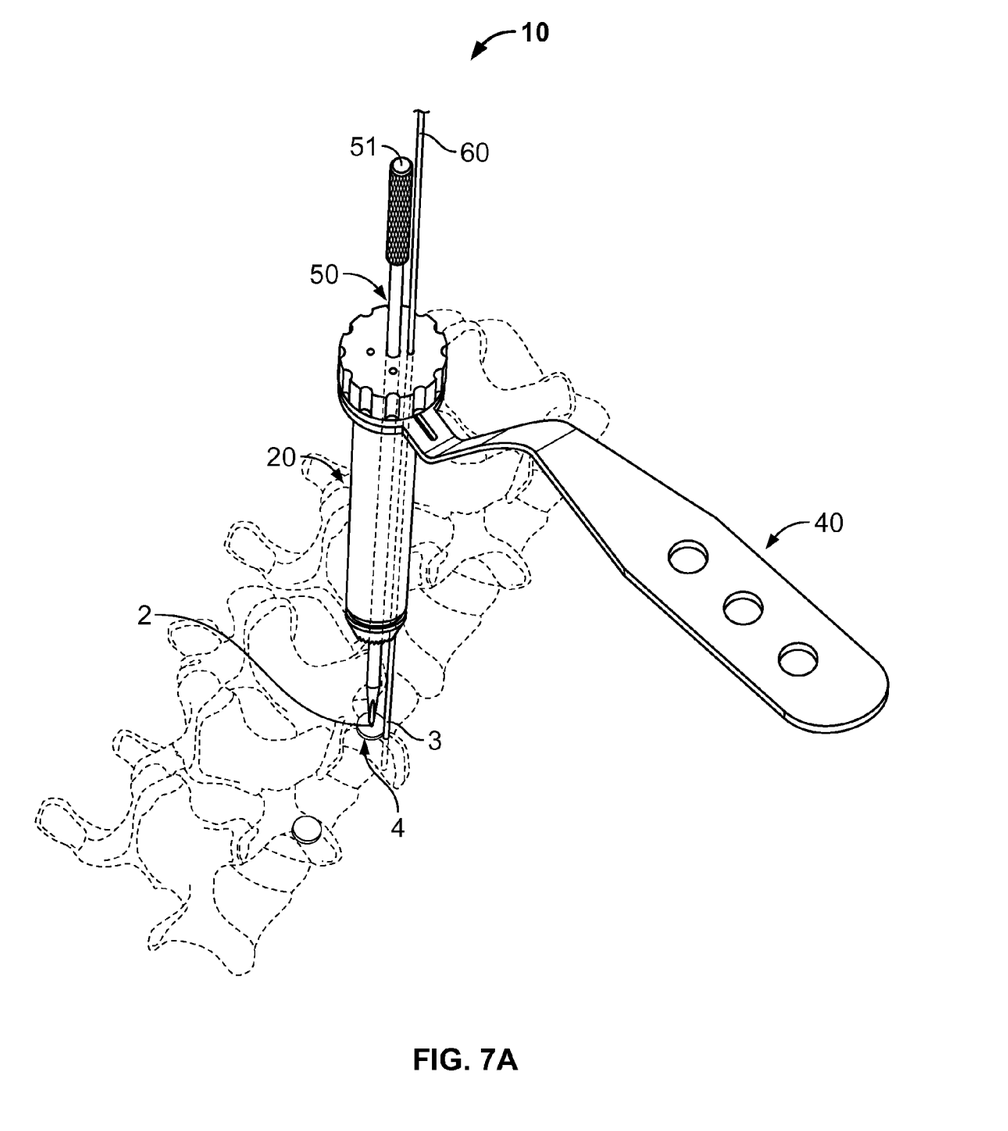
FIG. 7A is a similar view as FIG. 7, but with the entire guide body illustrated.
Figure 7B:
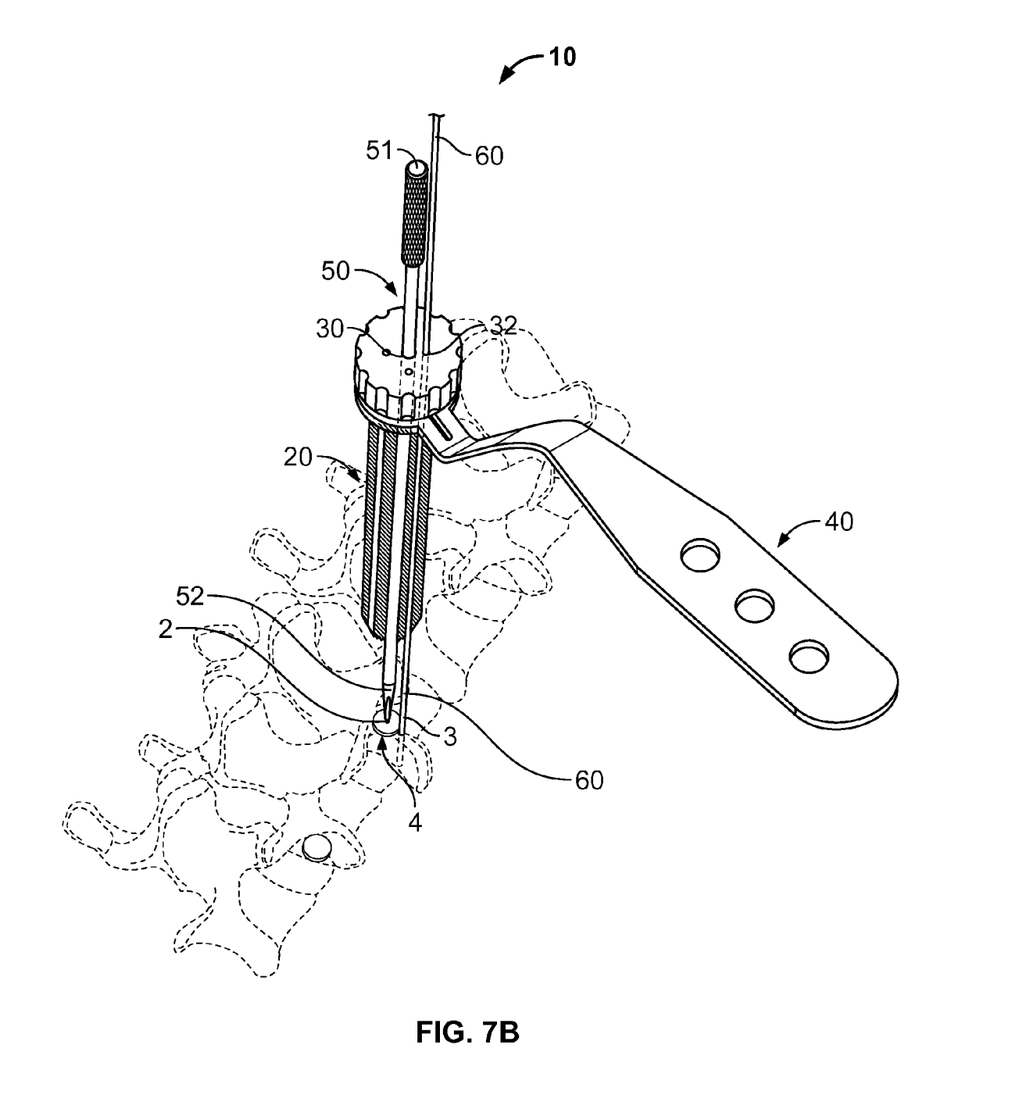
FIG. 7B is a view similar to FIG. 7A, but with the guide body mostly shown in a cross sectional view.
Figure 8:
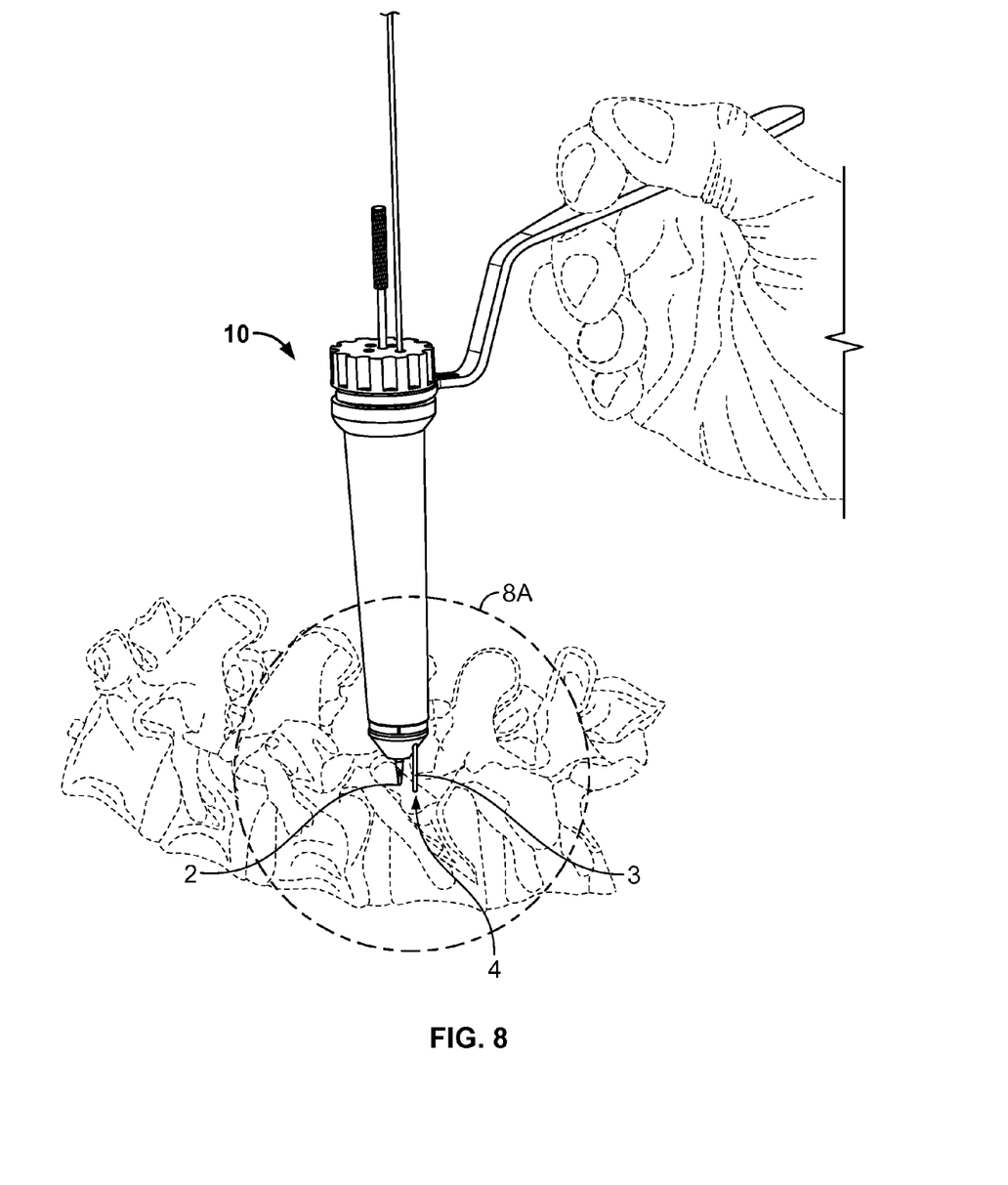
FIG. 8 is a lateral or side view of the drill guide of the present invention positioned over the pedicle showing the surgeon's hand in dashed lines removed from the imaging field of view.
Figure 8A:
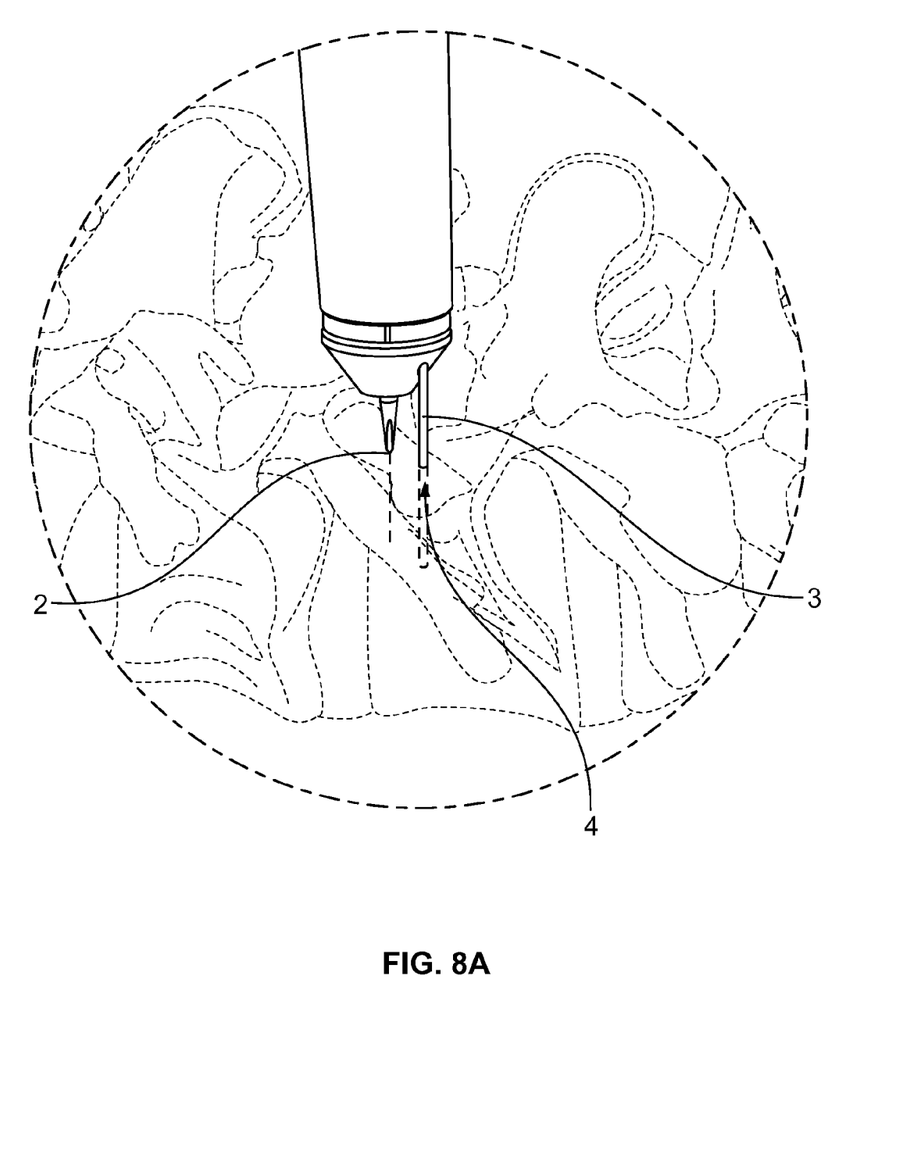
FIG. 8A is an enlarged view of the device of the present invention taken from the dashed circle 8A in FIG. 8.

With reference to FIG. 5, an exploded view of the Pedicle Drill Guide 10 make according to the present invention is shown. The guide device uses three main components, a radiolucent guide body 20, a handle 40 and a stabilizing anchor pin 50. Additionally, a radiopaque image marker or target ring 18 is provided that fits onto a slotted groove 28 on the guide body 20 near an inner tip end 22.

Figure 1:
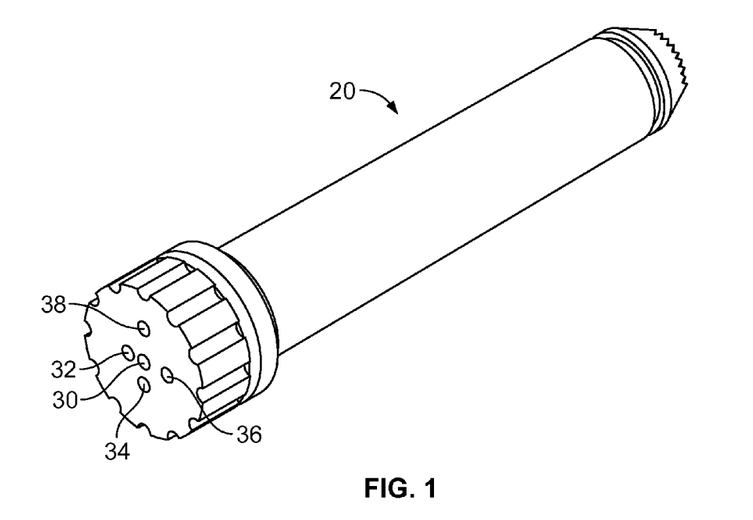
FIG. 1 is a perspective view of the guide body of Pedicle Drill Guide of the present invention.
Figure 1A:
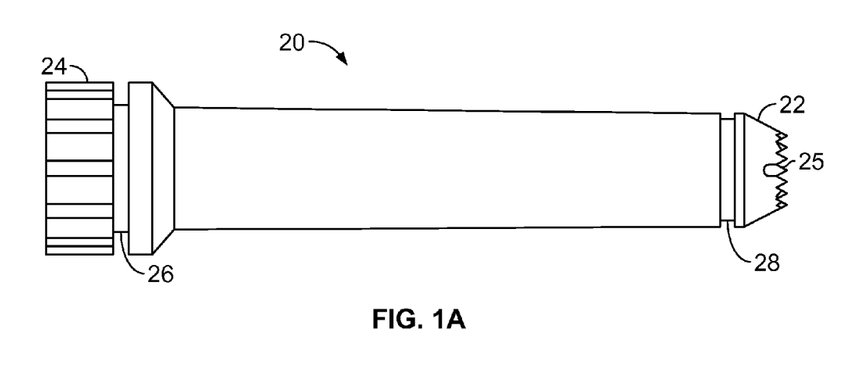
FIG. 1A is a plan or side view of the guide body.
Figure 1B:
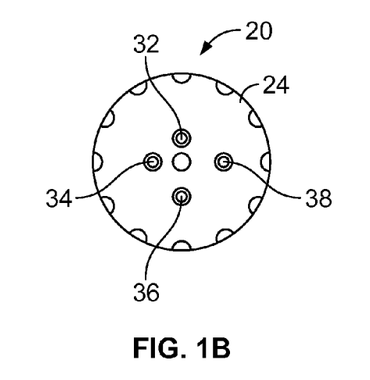
FIG. 1B is an end view of the outer end of the guide body.
Figure 1C:
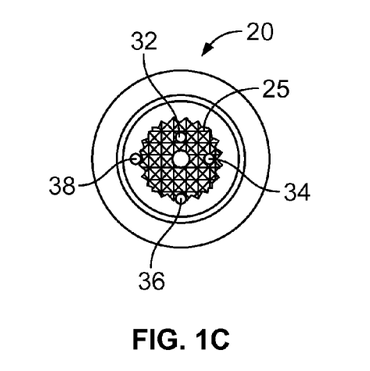
FIG. 1C is an end view of the outer end of the guide body.
Figure 1D:
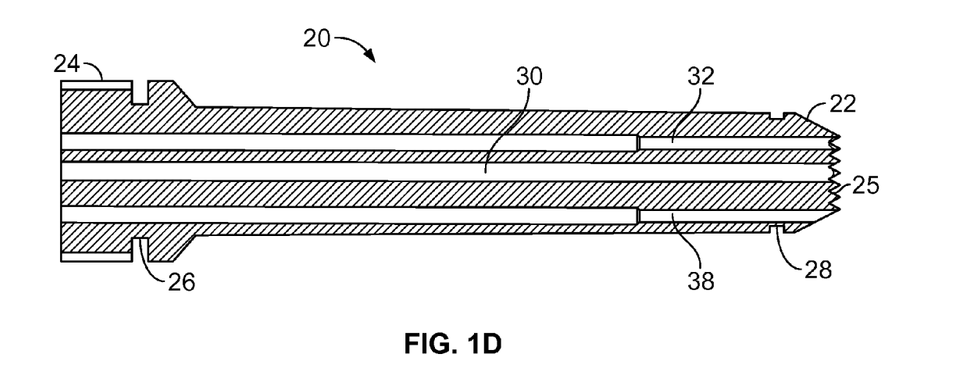
FIG. 1D is a cross sectional view of the guide body.

With reference to FIGS. 1, 1A, 1B, 1C and 1D various views of the guide body 20 are shown. In FIGS. 1, 1A and 1B the enlarged outer end 24 is shown. The enlarged outer end 24 has a knurled or notched surface to facilitate rotation of the guide body 20. The end of the outer end 24 of the guide body 20 shows a center hole 30. This center hole 30 is centered in the guide body 20 and extends through the outer end 24 along the guide body's 20 longitudinal length through the inner tip end 22. The hole 30 forms an axial shaft into which the stabilizing anchor pin 50 fits. The entire guide body 20 is able to rotate about the stabilizing anchor pin 50 which is precisely centered in the guide body 20. Around the center hole 30 are a plurality of satellite holes 32, 34, 36 and 38 as shown in FIGS. 1 and 1B. These satellite holes 32, 34, 36, 38 extend through the guide body 20 to through the inner tip end 22 as shown in FIGS. 1C and 1D. The satellite holes 32, 34, 36, 38 are spaced at distinct predetermined distances from the center or axis of the center hole 30. Preferably, the satellite holes 32, 34, 36, 38 are spaced in 1 mm increments such that the closest or first satellite hole 32 is 1 mm from the center hole 30, the second satellite hole 34 is 2 mm, the third satellite hole 36 is 3 mm and the fourth satellite hole 38 is 4 mm. It is believed that four satellite holes 32, 34, 36, 38 are optimum for adjusting screw location purposes, however more or less satellite holes can be used as long as there is provided a plurality of such holes for allowing proper alignment selections by the surgeon. The exit holes are parallel with the entry holes and are spaced the same distance apart along a radius from the center hole 30. Each entry hole is placed along a radius at 90 degrees from the next one to allow maximum flexibility for K-wire placement. Each entry hole is drilled at least about 1/16 inch to accommodate a 1/16 inch K-wire. In the cross sectional view, the entry hole portion of the satellite holes 32, 34, 36, 38 is shown of widely a larger diameter with the exit hole portion being sized to accommodate the K-wire. As used in this description, the satellite holes 32, 34, 36 and 38 are parallel to the center hole 30, by parallel it is meant the holes all extend longitudinally directionally in the same way in the guide body 20 within understood manufacturing tolerance. As such the satellite holes can have some angular variations from true parallel, but ideally are close to parallel so the screw placement and alignment will be as intended by the surgeon. As shown, the guide body 20 is shaped as a generally round cylindrical shaped component having a length sufficient to accommodate a large obese patient where penetration depth to the vertebrae can be several inches. As shown, the exemplary guide body as illustrated has a total length end to end of 4.375 inches with the enlarged outer end 24 occupying 0.75 inches of the length and having a diameter of 1.0 inches and the inner tip end 22 extending 0.25 inches of the total length. The tip end 22 maximum diameter is 0.66 inches and the guide body 20 tapers increasing in diameter to 0.72 inches near the outer end 24 to facilitate molding. The spiked inner tip end is substantially perpendicular to the length and has a diameter of about 0.5 inches. This rather compact size and shape enables the device to function in a small incision through the tissue minimizing surgical trauma.

An added feature shown in the figures is the use of a traction or grip surface at the inner tip end 22. A plurality of pointed projections 25 are provided to help stabilize the drill guide device 10 against the bone structure to reduce the occurrence of slippage. At the enlarged outer end 24 a grooved handle slot 26 is shown onto which the handle 40 can be clipped to secure the handle 40 to the guide body 20.

Figure 2:
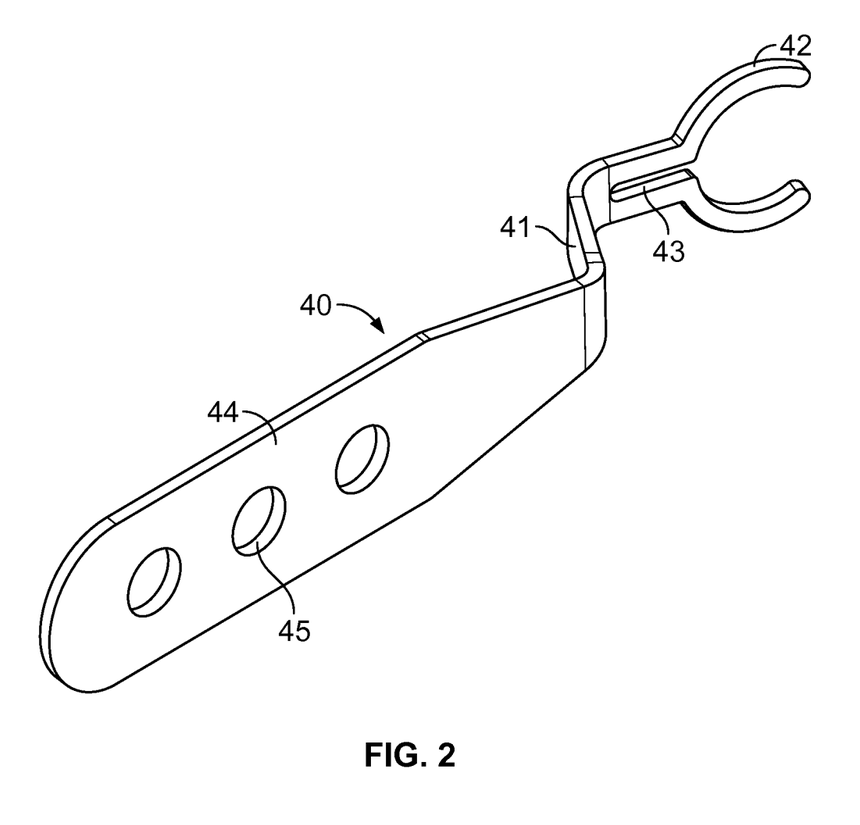
FIG. 2 is a perspective view of the handle of the Pedicle Drill Guide.
Figure 2A:
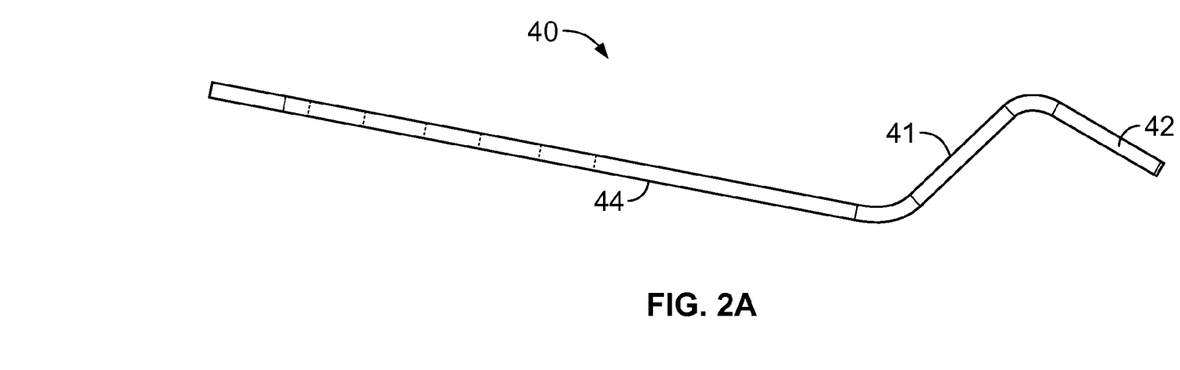
FIG. 2A is a side view of the handle.
Figure 2B:
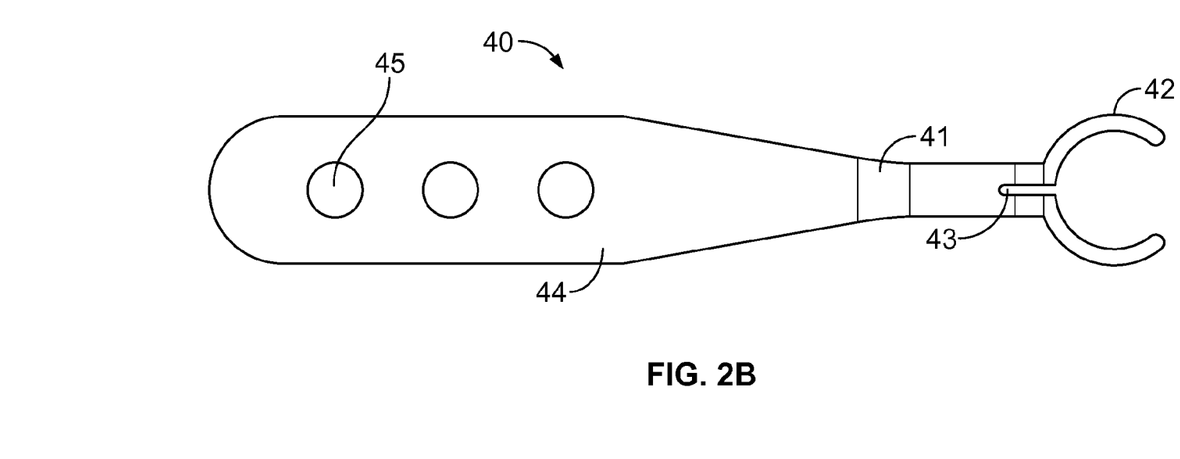
FIG. 2B is a top view of the handle.

With reference to FIGS. 2, 2A and 2B a handle 40 is illustrated. The handle 40 has a hand grasping portion 44 shown with holes 45 for weight reduction, a bend portion 41 extending from the portion 44 and a pair of guide gripping tines 42 which are sized to spread and snap into the grooved slot 26 of the guide body 20. The handle 40 as shown can be easily snapped onto the guide body 20 and can just as easily be removed from the guide body 20. When attached to the guide body 20 the handle 40 allows the surgeon to hold the device removed from the field of view when imaging the location. This has the added benefit of keeping the surgeon's hand out of the x-ray field. The guide body 20 when in the handle 40 or separated from the handle 40 is freely rotatable about the axis of the stabilizing pin 50. As shown, the handle 40 is very compact in size and has a total horizontal length of only 5.88 inches or slightly less than 6 inches. The grasping portion is only 3.8 inches or slightly less than 4 inches. What is greatly advantageous is the bend portion 41 along with the gripping tines 42 form an include angle of 100 degrees, the bend portion being about 0.82 inches vertically and 0.84 inches horizontally extending away from the gripping portion 41 allows the surgeon's hand to be vertically elevated and horizontally shifted out of the imaging field during the procedure. This feature reduces the hand exposure to harmful radiation and keeps the guide body 20 in the desired imaging field totally unobstructed.

Figure 3:
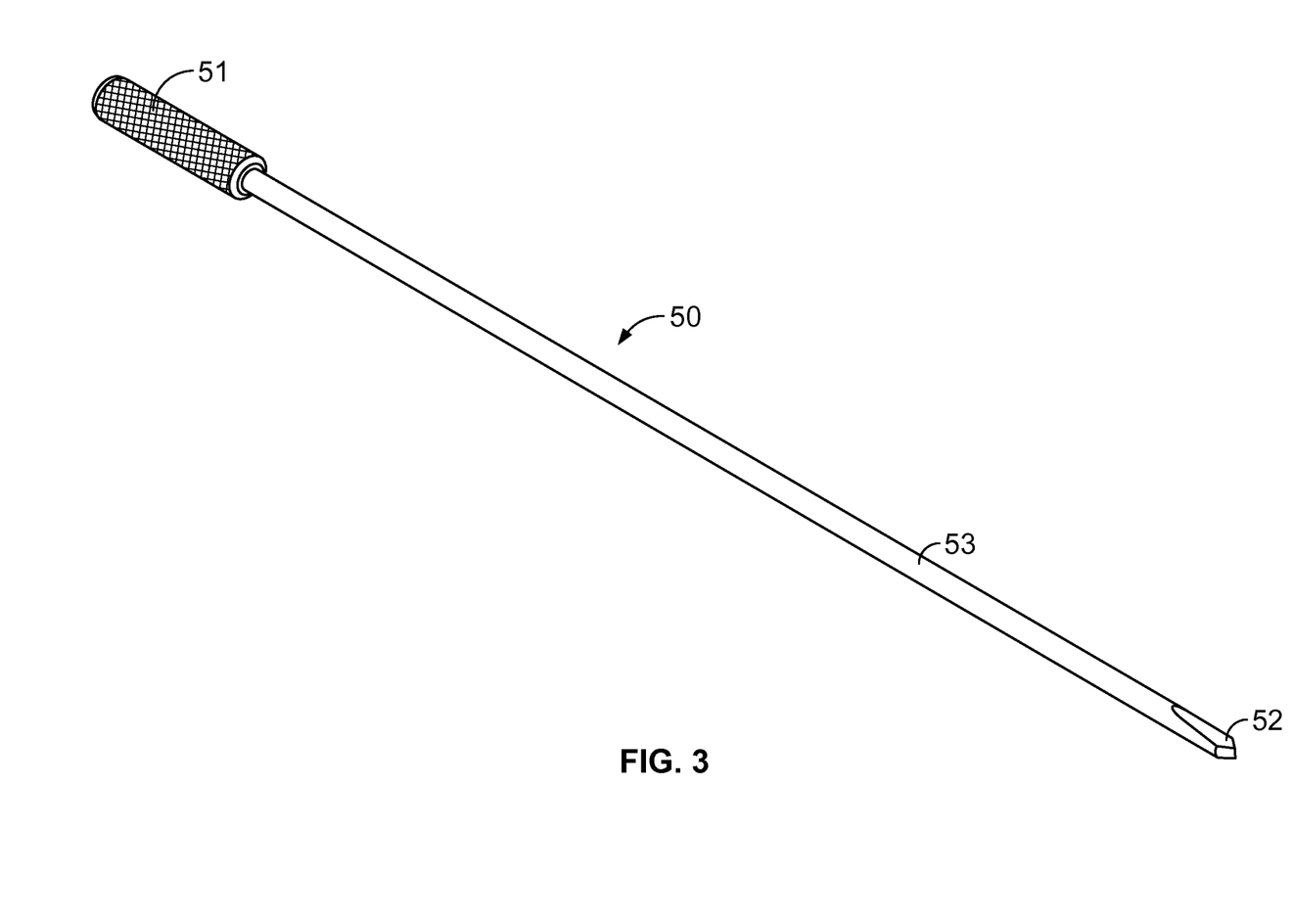
FIG. 3 is a perspective view of a stabilizing anchor pin used in the Pedicle Drill Guide.
Figure 3A:
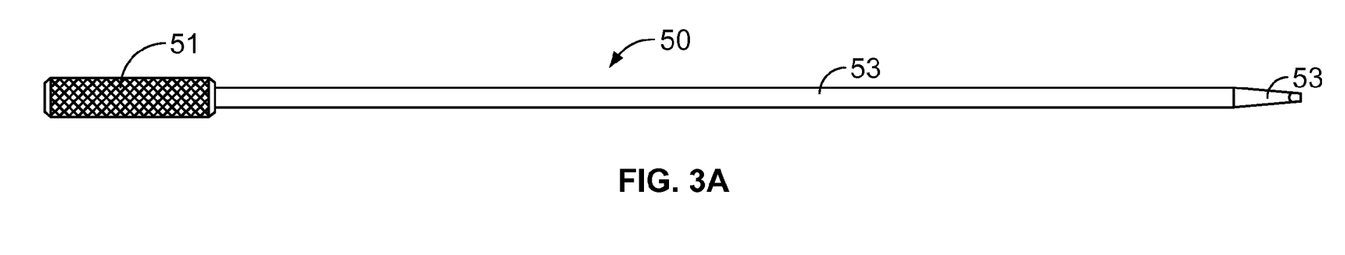
FIG. 3A is a side view of the stabilizing anchor pin.
Figure 3B:
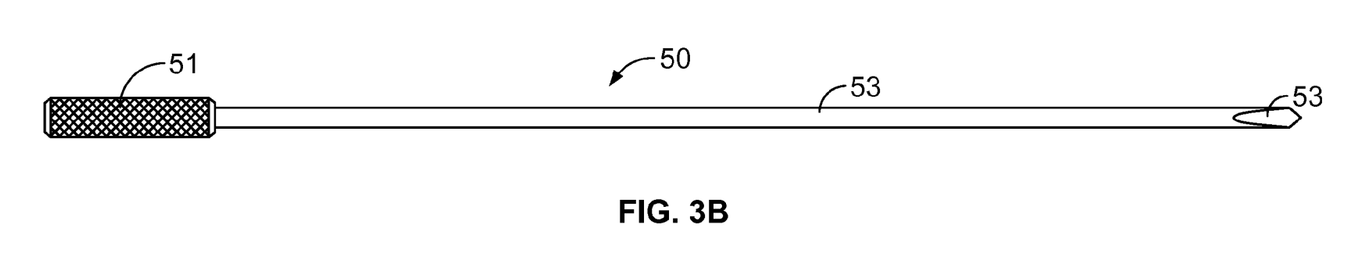
FIG. 3B is a top view of the stabilizing anchor pin.

With reference to FIGS. 3, 3A and 3B the initial stabilizing pin 50 is shown. The stabilizing pin 50 can be made from any sufficiently strong sharp pointed material. As shown, one head end 51 is enlarged and knurled to enable impact insertion or rotational drilling of the pin 50 into the bone. As illustrated, the stabilizing pin 50 was made from a larger K-wire having a 3/32 inch diameter and made longer than the guide body 20 so it can be tapped into bone through the guide. It has the larger head end 51 sized so that it cannot go through center hole 30 of the guide body 20 too deeply and the head end 51 also can facilitate handling.

Figure 4:
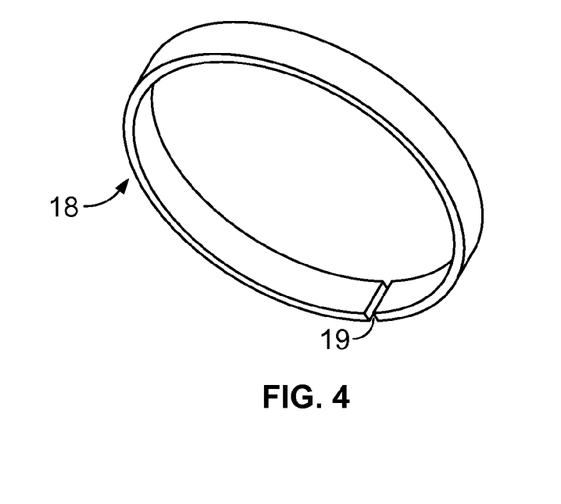
FIG. 4 is a perspective view of an image target ring for the Pedicle Drill Guide of the present invention.
Figure 4A:
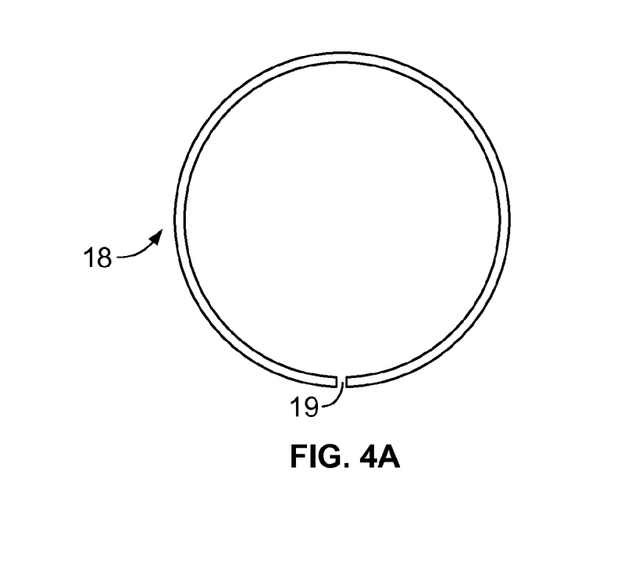
FIG. 4A is an end view of the target ring.
Figure 4B:
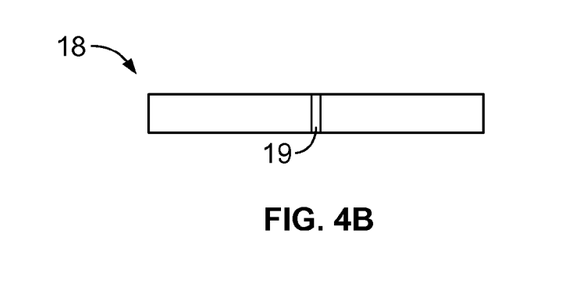
FIG. 4B is a side view of the target ring.

With reference to FIGS. 4, 4A and 4B a target marker ring 18 is shown. The ring 18 is made of a radiopaque material so that it stands out during x-ray imaging. The ring 18 has a slot 19 cutting across the ring 18 allowing the ring to expand and snap into the groove 28 of the guide body 20. Once in place, the ring 18 provides the surgeon an image visible indication of the location of the guide body 20 in the patient. This in combination with the initial stabilizing pin 50 provides an ideal locating feature which is explained in reference to FIGS. 7, 7A, 7B, 8 and 8A.

Typically the during operative use, the initial stabilizing pin 50 is placed at or near the center of the pedicle on the AP view and tapped into bone of the facet joint. The guide is then rotated to align one of the holes with the K-wire 60 inserted (3) to align it with the "3 o'clock" or far lateral position (4) of the pedicle on the AP view. Next the on lateral view the guide 10 is rotated to align one of the satellite holes 32, 34, 36 or 38 at 1, 2, 3 or 4 mm respectively with the correct position for midline lateral pedicle entry (3) on the Lateral view. By rotating the guide 10 slightly the K-wire alignment can be adjusted superiorly or inferiorly to align it with the mid pedicle line. The result should place the K-wire in a perfect position for pedicle broaching. The K-wire is then power drilled into the pedicle and vertebral body (4) with a pin driver commonly used in orthopedic surgery. The guide is angled radially as necessary to correspond to the normal lateral direction or axis of the pedicle, approximately 15 degrees.

During regular open and minimal invasive spinal surgery (MIS) the vertebral pedicle can be very difficult to cannulate so that a guide wire can be inserted into the vertebral body. It is important to precisely place the guide wire into the pedicle to provide a pathway for cannulated pedicle screw. Often multiple attempts are made with a Jamshidi needle using both AP and Lateral fluoroscopic views. Another anatomic challenge is that the entry point is a facet joint that is often dome shaped making it difficult to stabilize the Jamshidi needle prior to insertion.

The drilling guide body 20 is a radiolucent device which allows preliminary positioning of a needle/trochar near the center or lateral portion of the pedicle in the AP view and adjusting the final position of the lateral view without changing the initial position of the AP position. This guide 10 allows simultaneous alignment of both AP and Lateral views for ultimate ideal or perfect pathway for the pedicle cannulization.

Instead of using cumbersome Jamshidi needles, the pedicle is broached with a K-wire which is inserted with a power drill. This is only possible by exact positioning provided by the drilling guide 10. With the drilling guide 10 stabilized, this eliminates the K-wire from slipping off the facet joint and potentially missing the pedicle entirely. Power drilling with a pin driver allows very easy pedicle broaching and precise insertion into the vertebral body the first time. As a side benefit, the drilled in K-wire is much more-stable during tapping so that it doesn't unexpectedly become dislodged with the tapping procedure.

Currently no drill guide exists for use with spinal surgery to facilitate insertion of a guide wire or pedicle screw.

During spinal instrumentation surgery the vertebral pedicle is usually cannulated with a Jamshidi needle through a small incision and after dilators are inserted to spread out the paraspinal muscle fibers. This technique allows percutaneous access to the facet joint and ultimately the pedicle to be broached.

Often at this point begins a somewhat tedious procedure of lining up the Jamshidi needle with the pedicle on both AP and Lateral views of the C arm or x-ray fluoroscope. The typical technique recommends lining up the needle at the "3 o'clock" or far lateral position of the pedicle on the AP view (for a Right L4-5 pedicle for instance) while positioning the needle at the mid-pedicle line on the lateral x-ray view. Unless 2 C arms are utilized where one has simultaneous AP and Lateral views, this can become a very cumbersome process of trial and error. Anyone who has attempted this with one C arm knows how difficult it can be to place the needle at the correct starting position in both AP and Lateral views, not to mention the multiple C arm changes needed.

Alternatively, 2 C arms can be used but usually multiple repositions of the Jamshidi needle are necessary in order to start the needle in the correct position for lateral-to-medial. direction of the pedicle in the AP view combined with the down-the midpoint of the pedicle on the lateral view.

Another anatomic challenge is the fact most facet joints are domed shaped where the needle is started. This encourages slipping of the needle during insertion and may allow the needle to go in the wrong direction or miss the pedicle entirely. Sometimes the facet has sclerotic bony overgrow which makes the initial penetration point difficult. Occasionally the bony facet along with hard dense overgrow makes the needle insertion next to impossible without very hard pounding with a mallet.

Although, 2 C arms can facilitate needle insertion, the procedure usually requires multiple needle repositions (or trial and errors) to get it right. The additional C arm at the very least doubles the amount of radiation delivered to the patient and entire operating team as well as frequently getting in the way.

Finally, the Jamshidi needle is rather large in diameter and can even crack the pedicle in some circumstances since it is inserted much like a large nail. If the track created by the Jamshidi broaches the spinal canal it may be very difficult to redirect a better pathway without falling back into the original hole.

All of these problems can make pedicle cannulization very time consuming and frustrating. A better technique could save a lot of time and money as well as reducing the amount of radiation delivered to patient and team.

The new drill guide 10 allows an easy guide for drilling into the pedicle for a very accurately placed guidewire using only very few x-ray fluoroscopic shots. Thus, this can dramatically speed up the surgical process with much less radiation exposure.

All 3 main elements are required for the system to work properly.

All of the 3 main components connect together as illustrated in FIGS. 7, 7A, 7B, 8 and 8A.

The guide body 20 provides multiple entry drill holes referenced off a large center stabilizing anchor 50. Handle 40 allows the surgeon to position and stabilize the guide and helps keep his hands out of the x-ray field. It also can be interchangeable with additional guides if the more than one is used in a procedure. It is expected that the guide body 20 would be disposable but the handle could be re-sterilized. The center anchoring or stabilizing pin 50 of FIG. 3 facillates a stable reference point for subsequent K-wire insertion. It is anticipated that the guide 10 would be used for each pedicle broached for each pedicle screws needed by way of example, 4 pedicle screws for a one level fusion and 6 screws for a 2 level fusion and so on.

The handle 40 can be machined from aluminum and finished with typical finishes for surgical instruments. The guide body 20 can be machined or molded from plastic such as high density polyethylene or polypropylene.

The components are designed to work together for each pedicle entry. It is possible to interchange additional plastic guides for a subsequent procedure using a re-sterilized handle. Because of the softer nature of the plastic guide it should not be reusable due to some wear and tear and would probably best be disposable. The entire device could also be used in regular "open" or larger incision surgeries as well as other situations where pedicle targeting is needed (i.e. vertebroplasties and biopsies of a vertebrae).

This invention is designed to facilitate pedicle targeting during spinal surgery. A proposed preferred method of its use is explained as follows.

The patient is prepared for spinal surgery. For optimal efficiency in using the drill guide simultaneous AP and Lateral C arms are positioned preoperatively. Skin markings are made just lateral to the pedicles prior to the skin prep.

Typically 2 small parallel incisions are made on each side of the midline just lateral to the intended pedicle that is to be instrumented.

Sharp and blunt dissection are used along with dilators to expose the vertebrae down to the facet joint and desired pedicle that is to be cannulated. The opening created needs to be large enough to accommodate the drill guide 10 making sure that the drill guide end tip 22 rests firmly on the facet joint and not in soft tissue. The dissection can be aided by rotating a dilator tube in a circular fashion to help displace any soft tissue dorsal to the facet.

The drill guide 10 guide body 20 is then inserted in the opening and pathway created so that it rests firmly on the bony element of the facet joint just lateral of the pedicle center. In many cases it is possible to palpate with the drill guide tip end 22 where the lateral border of the facet drops off. The drill guide body 20 is then rested on the just lateral to the center of the pedicle as judged by the AP fluoro view.

The drill guide has the centering stabilizing anchor pin 50 positioned in the AP view between the pedicle center and the lateral pedicle wall. The guide body 20 centering and holding the pin 50 is angled approximately 15 degrees medially depending on pedicle anatomy. Once the pin 50 is positioned it is tapped into bone a few millimeters so it doesn't move.

Next on the lateral view align the centering stabilizing anchor pin 50 near the pedicle. The radiopaque ring 18 needs to overlap the center of the pedicle so that one of the guide satellite holes 32, 34, 36, or 38 will align with the pedicle center.

Next position a sharp K-wire 60 in one of the 4 channels so that it lines up with the most lateral border of the pedicle and facet. At this point the guide body 20 should be angled approximately 15 degrees medially depending on the anatomy as determined preoperatively.

Rotate the drill guide body 20 so that the K-wire 60 aligns with the approximate center axis of the pedicle on the lateral view. Adjust tilt angle of the body 20 so that it is parallel to the pedicle center.

Next Insert the K-wire 60 with a power pin driver into the pedicle and vertebral body. Make sure to go only ⅔ way toward the anterior margin of the vertebrae. EMG testing can now be performed if desired as the drill guide body 20 insulates the K-wire 60 from surrounding tissues.

One technical note: With the K-wire 60 partially inserted through the pedicle and entering the vertebral body on the lateral view, it should still be lateral to the medial pedicle wall on the AP view. Going beyond the medical pedicle wall at this point should be avoided.

For S-1 start lateral with the guide pin near the lateral pedicle wall and angle the K-wire toward the medial pedicle wall.

Finally a cannulated hand awl or limited depth drill may be required so that the screw tap can be easily engaged into bone especially in patients with harder bone. Other options are aggressive taps with a cutting flute tip.

Tapping of the screw holes can begin at this point. The use of tapered self-tapping screws may eliminate this step. Tapping should be only performed only ½ way or no deeper than 15 mm from the K-wire tip to avoid dislodging the K-wire prematurely. The K-wires usually have slight retention into bone since they are drilled in to the vertebral body making it easier to remove the tap without pulling out the K-wire.

It is preferred to remove the K-wire when the screw is only partially inserted (half way) since it can bind or kink the Kwire tip making it difficult to remove.

It is also preferred to place all the K-wires prior to laminectomy/decompression, if possible, as the drill guide is more stable on an intact facet joint and lamina.

The cannulated drill guide can help facilatate very quick and accurate placement of K-wires into the pedicles to be instrumented using minimal invasive fusion techniques.

It can help avoid difficult and sometimes traumatic placement using Jimshidi needles which can easily violate the pedicle walls.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A pedicle drill guide for use in spinal surgery to position and cannulate a vertebral pedicle, the drill guide comprising:
    a stabilizing anchor pin for securing into a pedicle offset from a pedicle center positioned between the pedicle center and a lateral pedicle wall;
    a molded radiolucent one piece guide body not suitable for autoclave sterilization wherein the guide body near an inner tip end has a truncated conical shaped tip for insertion into a surgical opening above the spine of the patient and resting firmly on a facet joint just lateral of the pedicle center, the inner tip end has a plurality of spiked projections for contacting the surface of the pedicle, the guide body made of a plastic or radiolucent material which allows x-ray imaging to pass and is heat sensitive unsuitable for autoclave sterilization to insure one time use, extending longitudinally from an outer end to the inner tip end, the guide body having a center hole for receiving a stabilizing anchor pin, the center hole extending longitudinally through the outer end and inner tip end, and a plurality of satellite holes extending through the guide body from inner tip end and outer end parallel to the center hole, each satellite hole having an entry hole portion of a larger diameter than an exit hole portion sized to accommodate a K-wire being spaced from the center hole by a distinct predetermined distance (d) and sized to receive the K-wire, the K-wire when inserted in a satellite hole for placement into a pedicle being at the distance (d) from an axial center of the center hole in which the stabilizing anchor pin is received and positioned offset from the pedicle center, the guide body being rotatable about the stabilizing anchor pin to allow positioning and alignment of the satellite hole relative to the pedicle center;
    a target ring affixed to the guide body near the inner tip end for overlapping the center of the pedicle, the target ring being a radio-opaque material to provide in combination with the stabilizing anchor pin an ideal locating feature to position one of the satellite holes with the pedicle center when precisely place the K-wire to provide a pathway for a cannulated pedicle screw, the guide allowing simultaneous alignment of both AP and Lateral views for positioning the K-wire pathway; and
    wherein the stabilizing anchor pin has a diameter larger than the K-wire and a length longer than the guide body by a few mm configured to secure the anchor pin to the facet joint.

2. The pedicle drill guide for use in spinal surgery to cannulate a vertebral pedicle of claim 1 wherein the body has at least 2 satellite holes.

3. The pedicle drill guide for use in spinal surgery to cannulate a vertebral pedicle of claim 1 wherein the body has at least 3 satellite holes.

4. The pedicle drill guide for use in spinal surgery to cannulate a vertebral pedicle of claim 3 wherein the plurality of satellite holes are spaced in 1 mm increments from the axial center of the center hole, the first satellite hole being at 1 mm distance (d), a second satellite hole at 2 mm distance ($d_2$) and a third satellite hole being at 3 mm distance ($d_3$).

5. The pedicle drill guide for use in spinal surgery to cannulate a vertebral pedicle of claim 3 wherein the plurality of satellite holes are spaced in 1 mm increments from the axial center of the center hole, the first satellite hole being at 1 mm distance (d), a second satellite hole at 2 mm distance ($d_2$), a third satellite hole being at 3 mm distance ($d_3$) and a fourths satellite hole at 4 mm distance ($d_4$).

6. The pedicle drill guide for use in spinal surgery to cannulate a vertebral pedicle of claim 1 wherein the body has at least 4 satellite holes.

7. The pedicle drill guide for use in spinal surgery to cannulate a vertebral pedicle of claim 1 wherein the plurality of satellite holes are spaced in 1 mm increments from the axial center of the center hole, the first satellite hole being at 1 mm distance (d), a second satellite hole at 2 mm distance ($d_2$).

8. The pedicle drill guide for use in spinal surgery to cannulate a vertebral pedicle of claim 1 further comprises:
    a removable handle with a split end for attachment to the guide body; and
    wherein the outer end of the guide body has an enlarged end with an outer gripping surface and a grooved channel adjacent the outer gripping surface for receiving the split end of the handle.

9. The pedicle drill guide for use in spinal surgery to cannulate a vertebral pedicle of claim 1 wherein the guide body is disposable and material of the guide body is selected to be heat sensitive and not suitable for autoclave sterilization.

10. The pedicle drill guide for use in spinal surgery to cannulate a vertebral pedicle of claim 1
    wherein the guide body has a target imaging grooved slot near a conical inner tip end to hold the target ring.

11. The pedicle drill guide for use in spinal surgery to cannulate a vertebral pedicle of claim 10 wherein the target ring is made of a radiopaque metallic material.

12. The pedicle drill guide for use in spinal surgery to cannulate a vertebral pedicle of claim 1 wherein the inner end has a plurality of spiked projections for contacting the surface of the pedicle.

13. The pedicle drill guide for use in spinal surgery to cannulate a vertebral pedicle of claim 1 wherein the satellite holes are configured with a portion of the hole near inner end closely sized to the diameter of K-wire to precisely position the K-wire.

14. The pedicle drill guide for use in spinal surgery to cannulate a vertebral pedicle of claim 1 wherein the diameter of the K-wire is 1/16 of an inch and the satellite hole at the inner end portion being closely sized to be at or near 1/16 of an inch to allow a slip fitment.

15. The pedicle drill guide for use in spinal surgery to cannulate a vertebral pedicle of claim 1 wherein the diameter of the satellite holes is larger from the outer end and extending toward an inner portion of the hole near the inner tip end.

* * * * *